US006340367B1

(12) United States Patent
Stinson et al.

(10) Patent No.: US 6,340,367 B1
(45) Date of Patent: *Jan. 22, 2002

(54) RADIOPAQUE MARKERS AND METHODS OF USING THE SAME

(75) Inventors: Jonathan S. Stinson, Plymouth; Claude O. Clerc, Eden Prairie, both of MN (US)

(73) Assignee: Boston Scientific Scimed, Inc., Plymouth, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/905,821

(22) Filed: Aug. 1, 1997

(51) Int. Cl.[7] .................................................. A61F 2/00

(52) U.S. Cl. ..................................................... 623/1.34

(58) Field of Search ................................ 623/1, 11, 12, 623/1.34; 606/194, 195

(56) References Cited

U.S. PATENT DOCUMENTS

| 4,202,349 A | 5/1980 | Jones .......................... 128/689 |
| 4,447,239 A | 5/1984 | Krütten ....................... 604/282 |
| 4,475,972 A | 10/1984 | Wong .......................... 156/167 |
| 4,655,771 A | 4/1987 | Wallsten ......................... 623/1 |
| 4,681,110 A | 7/1987 | Wiktor ......................... 128/343 |
| 4,693,237 A | 9/1987 | Hoffman et al. ................. 128/1 |
| 4,722,344 A | 2/1988 | Cambron et al. ............ 128/658 |

(List continued on next page.)

FOREIGN PATENT DOCUMENTS

| EP | 0183372 A1 | 6/1986 | |
| EP | 0679372 A2 | 11/1995 | |
| EP | 0709068 A2 | 5/1996 | |
| EP | 0689807 A3 | 8/1996 | |
| EP | 0775472 A2 | 5/1997 | |
| WO | 8002641 | 12/1980 | |
| WO | 9001969 | 3/1990 | |
| WO | 9004982 | 5/1990 | |
| WO | 9110766 | 7/1991 | |
| WO | 9216166 | 10/1992 | |
| WO | 9406372 | 3/1994 | |
| WO | 9406373 | 3/1994 | |
| WO | 9605872 | 2/1996 | |
| WO | 9640000 | 12/1996 | |
| WO | WO 97/11724 | 4/1997 | ........... A61L/27/00 |
| WO | WO 98/18408 | 5/1998 | ............. A61F/2/06 |

OTHER PUBLICATIONS

Advertisement for Spire Corporation radiopaque coating technology, Medical Products Manufacturing News, Mar. 1977, p. 30.

Studies on a new radiopaque polymeric biomaterial, A. Benzina, M.A.B. Kruft, F. Bar, F.H. van der Veen, C.W. Bastiaansen, V. Heijnen, C. Reutelingsperger, and L.H. Koole, Biomaterials 1994, vol. 15 No. 14, pp. 1122–1128.

Deformation Characteristics of a Bioabsorbable Intravascular Stent, C. Mauli Agrawal, Ph.D., PE. and Howard G. Clark, Ph.D., Investigative Radiology, Dec. 1992, vol. 27, pp. 1020–1024.

(List continued on next page.)

Primary Examiner—Michael J. Milano
(74) Attorney, Agent, or Firm—Larkin, Hoffman, Daly & Lindgren, Ltd.; Frederick W. Niebuhr, Esq.; Andrew D. Ryan, Esq.

(57) ABSTRACT

A temporary and retrievable radiopaque marker and discrete radiopaque marker for use on an implantable endoprosthesis. The elongate marker has a proximal end, a distal end, and a thickness. At least a portion of the marker is radiopaque and the marker is removably-attached to the implantable endoprosthesis.

57 Claims, 13 Drawing Sheets

U.S. PATENT DOCUMENTS

| | | | |
|---|---|---|---|
| 4,738,740 A | 4/1988 | Pinchuk et al. | 156/167 |
| 4,787,391 A | 11/1988 | Elefteriades | 128/654 |
| 4,954,126 A | 9/1990 | Wallstén | 600/36 |
| 4,968,317 A | 11/1990 | Törmälä et al. | 606/77 |
| 5,015,183 A | 5/1991 | Fenick | 433/76 |
| 5,024,232 A | 6/1991 | Smid et al. | 128/654 |
| 5,026,377 A | 6/1991 | Burton et al. | 606/108 |
| 5,047,050 A | 9/1991 | Arpesani | 623/1 |
| 5,059,211 A | 10/1991 | Stack et al. | 606/198 |
| 5,061,275 A | 10/1991 | Wallstén et al. | 623/1 |
| 5,085,629 A | 2/1992 | Goldberg et al. | 604/8 |
| 5,116,360 A | 5/1992 | Pinchuk et al. | 623/1 |
| 5,133,660 A | 7/1992 | Fenick | 433/76 |
| 5,133,742 A | 7/1992 | Pinchuk | 623/1 |
| 5,160,341 A | 11/1992 | Brenneman et al. | 606/198 |
| 5,163,951 A | 11/1992 | Pinchuk et al. | 623/1 |
| 5,177,170 A | 1/1993 | Sarpeshkar et al. | 528/76 |
| 5,201,757 A | 4/1993 | Heyn et al. | 606/198 |
| 5,203,777 A | 4/1993 | Lee | 604/280 |
| 5,229,431 A | 7/1993 | Pinchuk | 521/159 |
| 5,256,158 A | 10/1993 | Tolkoff et al. | 604/280 |
| 5,306,286 A | 4/1994 | Stack et al. | 606/198 |
| 5,320,602 A | 6/1994 | Karpiel | 604/54 |
| 5,346,981 A | 9/1994 | Sarpeshkar et al. | 528/85 |
| 5,354,257 A | 10/1994 | Roubin et al. | 600/7 |
| 5,366,504 A | 11/1994 | Andersen et al. | 623/11 |
| 5,405,402 A | 4/1995 | Dye et al. | 623/22 |
| 5,415,546 A | 5/1995 | Cox, Sr. | 433/213 |
| 5,423,849 A | 6/1995 | Engelson et al. | 606/191 |
| 5,429,617 A | 7/1995 | Hammersmark et al. | 604/264 |
| 5,433,727 A | 7/1995 | Sideris | 606/213 |
| 5,441,517 A | 8/1995 | Kensey et al. | 606/213 |
| 5,464,450 A | 11/1995 | Buscemi et al. | 623/6 |
| 5,464,650 A | 11/1995 | Berg et al. | 427/2.3 |
| 5,478,352 A | 12/1995 | Fowler | 606/213 |
| 5,484,444 A | 1/1996 | Braunschweiler et al. | 606/108 |
| 5,498,227 A | 3/1996 | Mawad | 600/3 |
| 5,500,013 A | 3/1996 | Buscemi et al. | 623/1 |
| 5,527,337 A | 6/1996 | Stack et al. | 606/198 |
| 5,545,208 A | 8/1996 | Wolff et al. | 623/1 |
| 5,551,954 A | 9/1996 | Buscemi et al. | 623/1 |
| 5,556,413 A | 9/1996 | Lam | 606/198 |
| 5,591,172 A | 1/1997 | Bachmann et al. | 606/108 |
| 5,591,222 A | 1/1997 | Susawa et al. | 623/1 |
| 5,591,224 A | 1/1997 | Schwartz et al. | 623/1 |
| 5,591,226 A | 1/1997 | Trerotola et al. | 623/1 |
| 5,609,627 A | 3/1997 | Goicoechea et al. | 623/1 |
| 5,624,411 A | 4/1997 | Tuch | 604/265 |
| 5,628,755 A | 5/1997 | Heller et al. | 606/108 |
| 5,628,787 A | 5/1997 | Mayer | 623/1 |
| 5,628,788 A | 5/1997 | Pinchuk | 623/1 |
| 5,630,840 A | 5/1997 | Mayer | 623/1 |
| 5,645,559 A | 7/1997 | Hachtman et al. | 606/198 |
| 5,653,747 A | 8/1997 | Dereume | 623/1 |
| 5,662,703 A | 9/1997 | Yurek et al. | 623/1 |
| 5,674,277 A | 10/1997 | Freitag | 623/1 |
| 5,674,286 A | 10/1997 | D'Alessio et al. | 623/11 |
| 5,676,146 A | 10/1997 | Scarborough | 128/654 |
| 5,683,449 A | 11/1997 | Marcade | 623/1 |
| 5,725,517 A | 3/1998 | DeBusk | 604/362 |
| 5,725,567 A | 3/1998 | Wolff et al. | 623/1 |
| 5,725,572 A | 3/1998 | Lam et al. | 623/1 |
| 5,741,327 A | 4/1998 | Frantzen | 623/1 |
| 5,762,625 A | 6/1998 | Igaki | 604/8 |

OTHER PUBLICATIONS

Studies on radio–opaque polymeric biomaterials with potential applications to endovascular prostheses, M. Kruft, A. Benzina, R. Blezer, and L. Koole, Biomaterials 1996, vol. 17, No. 18, pp. 1803–1812.

Advertisement for radiopaque polymers for medical device manufacturing, New England Urethane, Inc.

Gianturco–Roubin Flex–Stent GRII, M–D–D–I Report—"The Gray Sheet", Mar. 4, 1996.

Seventh Complex Coronary Angioplasty Course, May 1996, p. 257.

Synthetic Biabsorbable Polymers, Thomas H. Barrows, Ph.D., High Performance Biomaterials, Szycher ed., pp. 243–257.

Wound Closure Biomaterials and Devices, C.C. Chu, J.A. von Fraunhofer, amd H.P. Greisler, CRC Press, Boca Raton, FL, 1997, pp. 131–235.

In Vitro Degradation of Polylactides Depending on Different Processes, M. Dauner, E. Muller, B. Wagner, and H. Planck, Degradation Phenomena on Polymeric Biomaterials, H. Planck, M. Dauner, M. Renardy (eds), Springer–Verlag, Berlin, 1992, pp. 107–122.

Long–term in vivo degradation and bone reaction to various polylactides, P. Mainil–Varlet, B. Rahn, and S. Gogolewski, Biomaterials 1997, vol. 18, No. 3, pp. 257–266.

Current Status of Biodegradable Stents, J.F. Tanguay, M.D., J.P. Zidar, M.D., H.R. Phillips, III, M.D., and R. S. Stack, M.D., Cardiology Clinics, vol. 12, No. 4, Nov. 1994, pp. 699–713.

Perspectives on the In Vivo Responses of Biodegradable Polymers, James M. Anderson, M.D., Ph.D., CRC Press Inc., (1995) pp. 223–233, 1995.

Advances in Controlled Release Technology: Polymeric Delivery System for Drugs, Pesticides and Foods: New Methods of Drug Delivery, Robert Langer, Science vol. 249, pp. 1527–1533.

Advances in Controlled Release Technology: Polymeric Delivery System s for Drugs, Pesticides and Foods: Fundamentals of pH. and Temperature–Sensitive Polymers, Nicholas A. Peppas, pp. 32–45.

Bioabsorbable Stent and Method of Making the Same, Assignee: Duke University.

Enhancement of the Mechanical Properties of Polylactides by solid–state extrusion, Walter Weiler and Sylwester Gogolewski, Biomaterials 17 (1996), pp. 529–535.

The Physics of Radiology, H.E. Johns and J.R. Cunningham, pp. 137–142.

Bicomponent vascular grafts consisting of synthetic absorbable fibers. I. In Vitro Study, Tarng–Jenn Yu and C.C. Chu, Journal of Biomedical Materoa;s Research, vol. 27, 1329–1339 (1993).

Biomedical Applications of Synthetic Biodegradable Polymers, Editited by Jeffrey O. Hollinger, D.D.S., Ph.D., CRC Press, p. 21.

Development of a Polymer Endovascular Prosthesis and Its Implantation in Porcine Arteries, William J. Van der Giessen, M.D., et al., Journal of Interventional Cardiology, vol. 5, No. 3, 1992, pp. 175–185.

Role of Polymers in improving the results of stenting in coronary arteries, Tao Peng, et al., Biomaterials 1996, vol. 17, No. 7, pp. 685–694.

Bioabsorbable, Drug–Eluting, Intracoronary Stents: Design and Future Applications, R.S. Schwartz, et al., Coronary Stents (1992), pp. 135–154.

Ten Years of Stenting: What Next?, Ulrich Sigwart, M.D., FRCP, FACC, FESC, Journal of Interventional Cardiology, vol. 10, No. 3, pp. 195–205.

Biocompatibility of solid poly (ortho ester), M. Ekholm, et al., Journal of Materials Science: Materials in Medicine 8, (1997), pp. 265–269.

The Polymer Stent, Jean–François Tanguay, et al., Endoluminal Stenting, pp. 216–225.

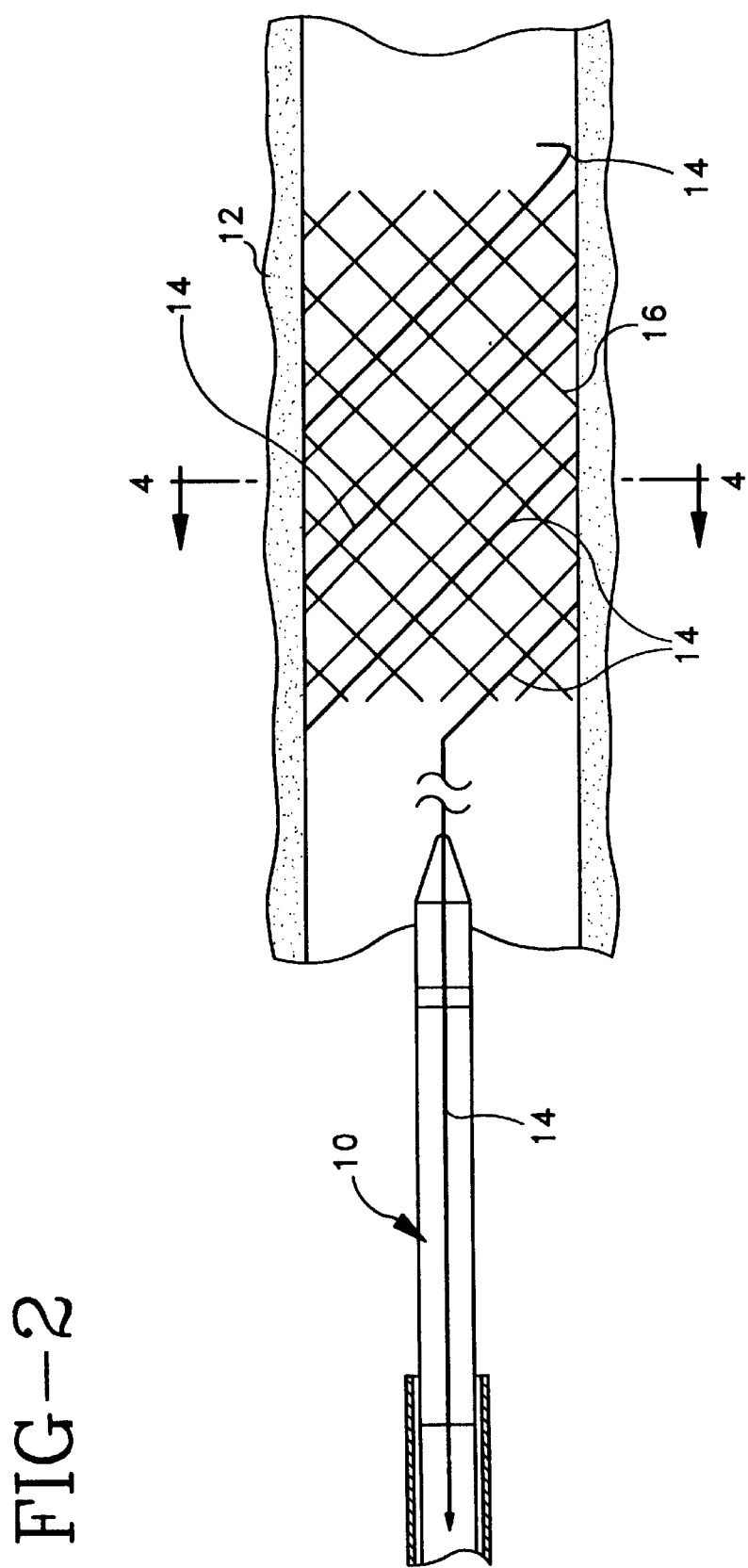

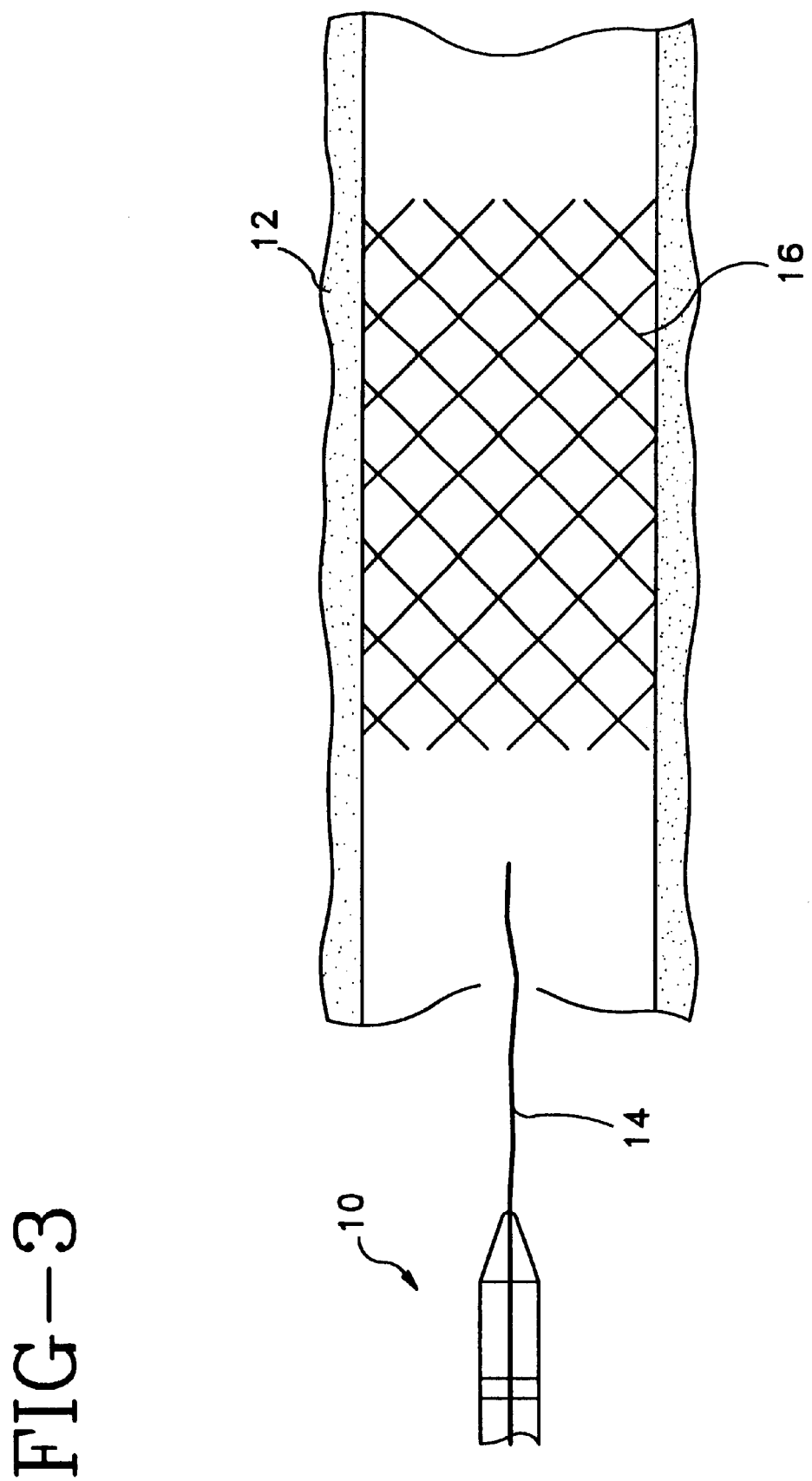

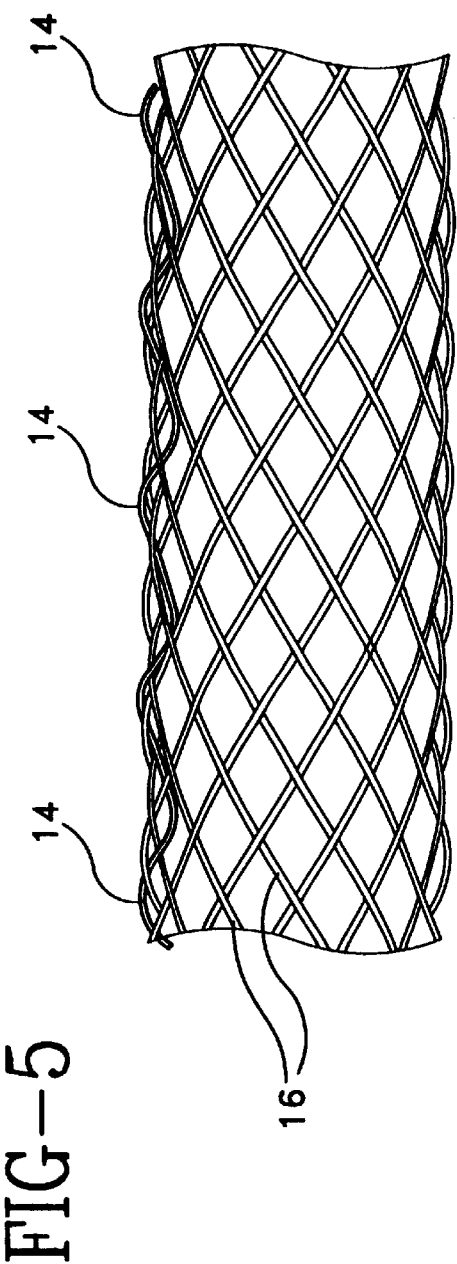
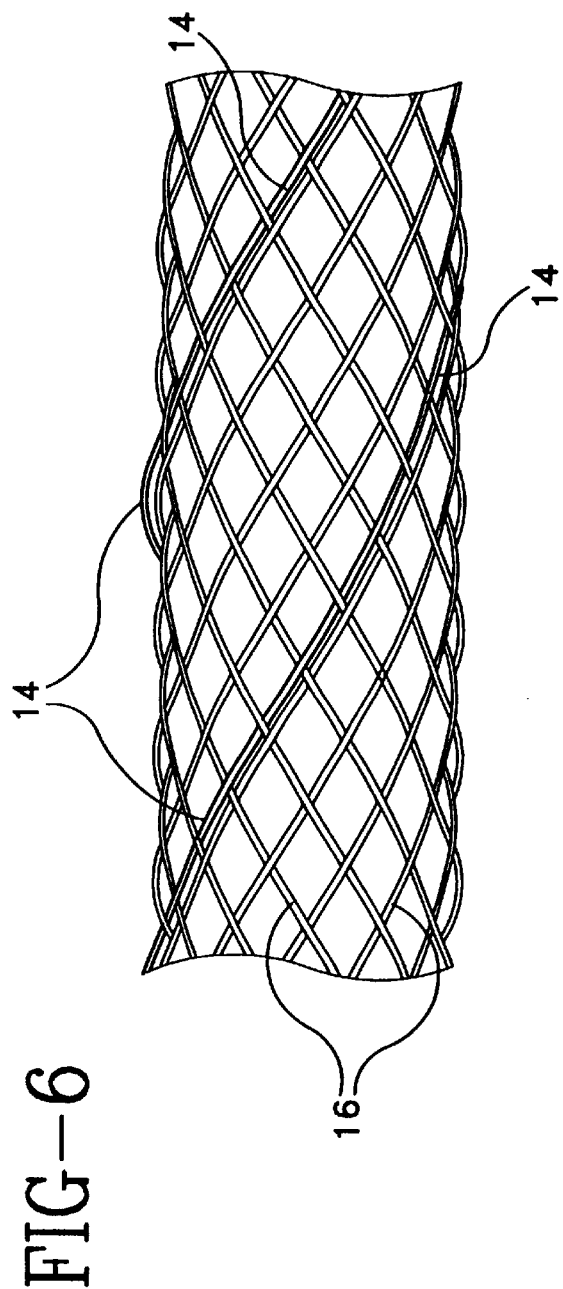
FIG-5
FIG-6

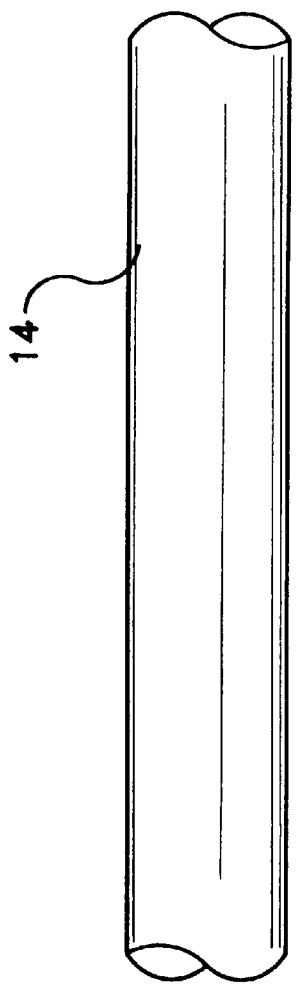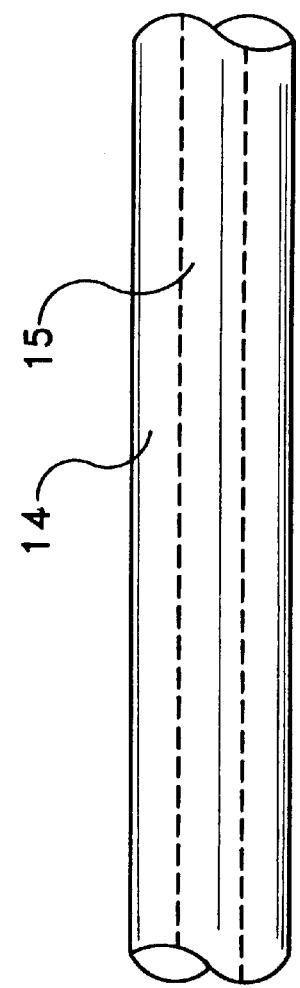
FIG-11a
FIG-11b

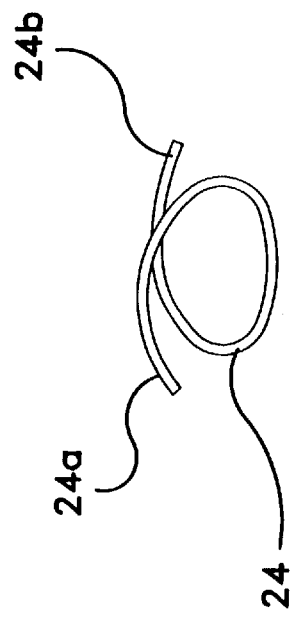
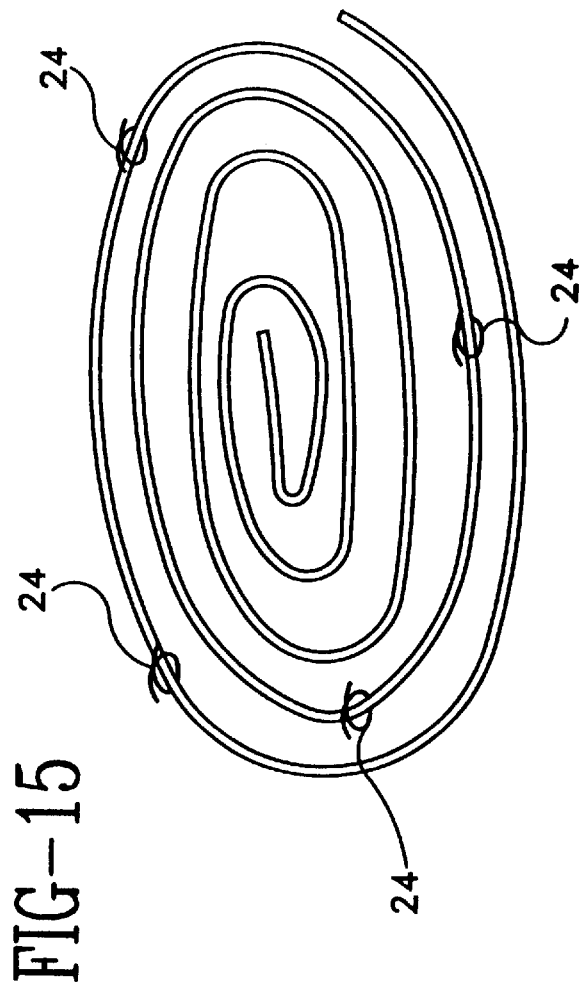
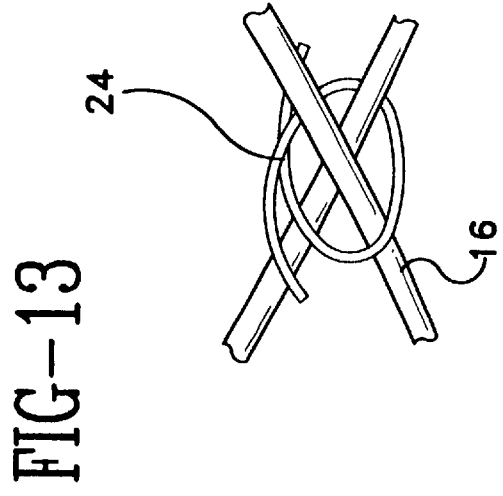

RADIOPAQUE MARKERS AND METHODS OF USING THE SAME

BACKGROUND OF THE INVENTION

This invention relates generally to a retrievable radiopaque marker or a discrete radiopaque marker for use on an implantable endoprosthesis such as a stent.

Implantable endoprostheses including stents, stent-grafts, and grafts are used in percutaneous transluminal coronary angioplasty and in other medical procedures to repair and support diseased or damaged arteries and body lumens. Grafts are implanted to cover or bridge leaks or dissections in vessels. Stent-grafts are stents which generally have a porous coating attachment and may be implanted by percutaneous transluminal angioplasty. Unsupported grafts are porous tubes which are typically implanted by surgical cut-down.

In order to visualize the passage and placement of the implantable endoprosthesis in arteries and body lumens, many surgical procedures are performed under fluoroscopy. The surgical delivery device and implantable endoprosthesis may be visualized if they are radiopaque and offer radiographic contrast relative to the body. For example, X-ray radiation may be used to visualize surgical delivery devices and deployment of the implant in the body. Also, radiographic contrast solution may be injected into the body lumen so that the lumen may be seen in the fluoroscopic image.

In order for an implantable endoprosthesis to be radiopaque, it must be made from a material possessing radiographic density higher than a surrounding host tissue and have sufficient thickness to affect the transmission of x-rays to produce contrast in the image. Reference is made to the clad composite stent shown in U.S. Pat. No. 5,630,840. An implantable endoprosthesis may be made of metals including tantalum or platinum having relatively high radiographic densities. Other metals such as stainless steel, superalloys, nitinol, and titanium having lower radiographic densities may also be used. Reference is made to implantable devices shown in U.S. Pat. Nos. 4,655,771; 4,954,126; and 5,061,275.

An implantable polymeric endoprosthesis is generally radiolucent and does not possess sufficient radiographic density to be easily imaged by fluoroscopy. To improve the imaging of polymeric materials, polymers may be mixed with radiopaque filler materials prior to molding or extruding in order to enhance the radiographic density. However, a disadvantage of using fillers with polymers is that changes in the properties of the polymer may occur. For example, the addition of fillers may reduce the strength or ductility of the polymer.

There is a need for an improved radiopaque marker for use in medical devices, particularly in temporary medical devices having low radiopacity. The need to improve the radiopacity of a relatively low radiopaque implantable endoprosthesis or improve imaging in low radiopaque conditions is particularly important for surgery, micro-surgery, neuro-surgery, and conventional angioplasty procedures performed under fluoroscopy. Physicians are constantly being challenged to place small implants at remote intraluminal locations.

Various devices having radiopaque markers are shown in U.S. Pat. Nos. 4,447,239; 5,423,849; and 5,354,257.

All documents cited herein, including the foregoing, are incorporated herein by reference in their entireties for all purposes.

SUMMARY OF THE INVENTION

Accordingly, there is a need for retrievable radiopaque markers for use in implantable endoprostheses to improve radiopacity and the locatability of endoprostheses in various medical procedures. Providing temporary radiopacity is especially advantageous for implantable endoprostheses having little or no radiopacity. The markers allow radiographic identification of one or more locations of interest on an implantable endoprosthesis. The locations of interest may include one or more covered or coated regions.

Alternative embodiments include threading the markers adjacent a helical strand in the implantable endoprosthesis, circumferentially around the implantable endoprosthesis, in a straight line in the axial direction of the implantable endoprosthesis, or disposing the wire in the form of pigtail-shaped rings, coils, or knots around filament crossing points in the implantable endoprosthesis.

Temporary retrievable radiopaque markers in the fabric or covering materials of an implantable endoprosthesis are advantageous for indicating the location of the fabric or covering during implantation. After implantation, the temporary retrievable radiopaque marker may be retrieved so as not to effect the function of the endoprosthesis.

A disadvantage of some permanent radiopaque markers is that they may compromise structural integrity, may not be biocompatible or biostable, and may be more thrombogenic than the implantable endoprosthesis.

The temporary retrievable radiopaque marker of the present invention advantageously allows most any implantable endoprosthesis to have temporary radiopacity over a predetermined portion of its structure, and assists with proper positioning and locatability of the implantable endoprosthesis in a body lumen.

Use of temporary retrievable radiopaque markers on an implantable endoprosthesis is advantageous because the radiopaque property may be present only for a desired time period. Generally, radiopacity is most desirable during placement of the implant. Once the implantable endoprosthesis is implanted, it may be more desirable to image the device with techniques such as ultrasound, magnetic resonance, and endoscopy and avoid further radiation exposure to the patient. Temporary radiopacity may be made by incorporating non-integral, retrievable radiopaque constituents into the implant. Thus, light metals, thin radiopaque metals, polymers, and ceramics may be utilized for a wide range of properties and flexibility in design of the endoprosthesis.

Attenuation is the change in the number of photons in the incident x-ray beam due to the interaction with an absorber. To image an object implanted in the body, it would be desirable to have the object attenuate x-rays more than body tissue, bone, and fat so that the difference in contrast will be obvious in a radiograph. The difficulty in selecting a radiopaque material for surgical implants is that the material must have desirable radiographic characteristics and biocompatibility.

In order to make an implant more radiopaque, a substance which absorbs more x-rays can be deposited on or mixed in with the implant material. If the implant absorbs more x-rays than the surrounding medium (for example tissue in the body), it will be visible as a sharp change in contrast on an x-ray film or fluoroscopy image.

The fraction of x-ray energy transmitted through the absorber is quantitatively predicted by the following equation described in *The Physics of Radiology*, Fourth Ed., H. Johns, J. Cunningham, 1983, pp. 137–142.

$N = N_0 e^{-\mu x}$

N=number of photons transmitted through x $N_0$=number of photons in the incident beam $\mu$=linear attenuation coefficient of the absorber x=absorber thickness $N/N_0$ would be the fraction of incident x-ray energy that is transmitted through the absorber. A more radiopaque material would have a lesser fraction of transmitted energy than a more radiolucent material. Therefore, to enhance the radiopacity of a material, such as the marker material, it would be desirable to select a material with high x-ray absorbing capability to minimize the fraction of transmitted energy. This radiopacity capability is proportional to the linear attenuation coefficient and the thickness of the absorber material. The higher the attenuation coefficient of the absorber material for a given thickness, the more radiopaque the absorber will be. The attenuation produced by an absorber is dependent upon the number of electrons and atoms present in the absorber. One way of quantifying this absorption characteristic is with the atomic attenuation coefficient which is directly proportional to the linear attenuation coefficient and the atomic number of the absorber element. Radiopacity is therefore generally proportional to the atomic number (number of electrons in the atom) of the material. Candidate materials for enhancing the radiopacity of surgical implants would have higher atomic numbers than the elements present in the body and would have to be biocompatible. The atomic number must be sufficiently high so that relatively small thickness of absorber material can be used in the body. Reference is also made to linear attenuation coefficient described in U.S. Pat. No. 5,628,787. Reference is made to Table 1 which describes a number of elements and their respective atomic numbers and certain linear attenuation coefficients.

TABLE 1

| Element or Material | Atomic Number or Effective Atomic Number | Linear Attenuation Coefficient at 50 KeV, cm$^{-1}$ |
| --- | --- | --- |
| hydrogen | 1 | .000028 |
| carbon | 6 | .417 |
| fat | 6.46 | .1925 |
| water | 7.51 | .2245 |
| muscle | 7.64 | .2330 |
| air | 7.78 | .00025 |
| nitrogen | 7 | .00023 |
| oxygen | 8 | .00028 |
| bone | 12.31 | .5727 |
| titanium | 22 | |
| iron | 26 | 15.2 |
| cobalt | 27 | 18.8 |
| bromine | 35 | |
| zirconium | 40 | |
| iodine | 53 | 45 |
| barium | 56 | 58 |
| tantalum | 73 | 111 |
| platinum | 78 | 108 |
| gold | 79 | 101 |
| lead | 82 | 88.7 |
| bismuth | 83 | 62 |

The elements hydrogen, oxygen, carbon, and nitrogen are commonly found in the body and in polymers, so elements with higher atomic numbers than these should enhance the radiopacity of a polymer implant or marker. Tantalum, zirconium, titanium, barium, bismuth, and iodine are known to be non-toxic in certain concentrations and thus are candidate elements for enhancing radiopacity of a polymer marker in an implant. These elements can be added to the polymer in various loading percentages and the threshhold above which the loading causes unsatisfactory changes in the polymer characteristics can be determined through material and device testing. The elements which can be added in quantities sufficient to enhance radiopacity and maintain an acceptable level of polymer properties and which are biocompatible could be utilized in markers. The biocompatible elements with a range of atomic numbers from about 22 to about 83 and having linear attenuation coefficients in the range from about 10 to about 120 cm$^{-1}$ at 50 KeV should provide enough enhancement in radiopacity without excessive thickness being necessary to be useful in markers. These elements would include at least titanium, vanadium, chromium, iron, cobalt, nickel, copper, bromine, zirconium, niobium, molybdenum, silver, iodine, barium, tantalum, tungsten, platinum, gold, and bismuth. The preferred metallic elements for biocompatibility and radiopacity are titanium, zirconium, tantalum, and platinum. The preferred organic elements for biocompatibility and radiopacity are bromine, iodine, barium, and bismuth. Especially preferred elements are tantalum, platinum, barium, and bismuth because of their high atomic numbers and biocompatibility (atomic numbers from 56 to 83 and linear attenuation coefficients from 30 to 120). Tantalum and platinum are used as stent components and barium sulfate and bismuth trioxide are used as radiopaque enhancements for polymer catheters.

In sum, the invention relates to an implantable endoprosthesis and radiopaque marker system. The system includes an implantable endoprosthesis adapted to be disposed in a body lumen and at least one elongate marker. The marker has a proximal end, a distal end, a thickness, and at least one radiopaque portion. The radiopaque portion includes a radiopaque material. The marker is removably attached to at least a portion of the implantable endoprosthesis and is removeable from the endoprosthesis when the endoprosthesis is in vivo. The radiopaque material may be at least partially dispersed from the marker over time. The radiopaque material may have a linear attenuation coefficient of from about 10 cm$^{-1}$ at 50 KeV to about 120 cm$^{-1}$ at 50 KeV. The thickness of the marker may range from about 20 microns to about 500 microns and the radiopaque material may have at least one element with an atomic number of from about 22 to about 83. The marker may include an oxide or salt material having at least one element with an atomic number of from about 22 to about 83. The marker may include barium sulfate, bismuth trioxide, iodine, iodide, titanium oxide, zirconium oxide, gold, platinum, silver, tantalum, niobium, stainless steel, or combinations thereof. The marker may be coated or alloyed with a radiopaque material that has a linear attenuation coefficient of from about 10 cm$^{-1}$ at 50 KeV to about 120 cm$^{-1}$ at 50 KeV. The marker may cross at least one portion of the implantable endoprosthesis. The marker may be a wire, mono-filament, multi-filament, ribbon, suture, spring, or combinations thereof. The marker may include metals, polymers, copolymers, ceramics, or combinations thereof. The marker may include at least one hollow, cavity, or porous portion. The marker may include at least one hollow, cavity, or porous portion therein adapted to receive the radiopaque material removably attached therein. The proximal end of the marker may be connected to at least one of the implantable endoprosthesis delivery device or a handle. The proximal end of the marker may have a hook, knob, ring, or eyelet attached thereto. The marker system may include a delivery device wherein the implantable endoprosthesis and marker are disposed in the delivery device and adapted for implantation into a body lumen. The implantable endoprosthesis may include a stent, stent-graft, graft, filter, occlusive device, or valve. The marker system may include at least one elongate wire removably attached to the implantable endoprosthesis wherein the marker crosses at least a portion of the implantable endoprosthesis and crosses the at least one elongate wire.

The invention also relates to an implantable endoprosthesis and radiopaque marker system. The marker system includes an implantable endoprosthesis adapted to be disposed in a body lumen and at least one elongate marker. The marker is removably attached to the implantable endoprosthesis. The marker has a proximal end, a distal end, a thickness, at least one hollow, cavity, or porous portion, and at least one radiopaque material having a linear attenuation coefficient of from about 10 $cm^{-1}$ at 50 KeV to about 120 $cm^{-1}$ at 50 KeV wherein the radiopaque material is removably attached to at least one of the hollow, cavity, or porous portions. The radiopaque portion may include a liquid, solid, powder, gel, wire, mono-filament, multi-filament, pellet, particle, or combinations thereof.

The invention also relates to a method of marking an implantable endoprosthesis including removably-attaching at least one elongate marker having a proximal and distal end to a portion of an implantable endoprosthesis to form an assembly. The marker includes at least one radiopaque material having a linear attenuation coefficient of from about 10 $cm^{-1}$ at 50 KeV to about 120 $cm^{-1}$ at 50 KeV; disposing the implantable endoprosthesis and marker assembly in a delivery system; inserting the delivery system in a body lumen; deploying the implantable endoprosthesis and marker assembly from the delivery system into the body lumen; and removing at least a portion of marker from the implantable endoprosthesis. The method may further include performing one or more medical procedures using the markers as a surgical guide prior to removing at least a portion of the marker from the endoprosthesis. The marker may include a radiopaque portion and a secondary portion. The radiopaque portion is first substantially removed from the implantable endoprosthesis prior to removal of the remaining secondary portion of the marker. Removing the marker from the implantable endoprosthesis may be performed by a force controlled from outside the body. The method may further include removably-attaching at least one wire to at least a portion of the implantable endoprosthesis and crossing the wire or the elongate marker over the other such that one of the marker or the wire requires removal prior to removal of the other from the implantable endoprosthesis.

The invention also relates to an implantable endoprosthesis and radiopaque marker system. The marker system includes an implantable endoprosthesis having a tubular and radially expandable structure adapted to be disposed in a body lumen and at least one elongate marker. The marker is removably attached to the implantable endoprosthesis. The marker includes a radiopaque material having a linear attenuation coefficient of from about 10 $cm^{-1}$ at 50 KeV to about 120 $cm^{-1}$ at 50 KeV, a proximal end, a distal end, and a thickness. The radiopaque material disperses into the body when in vivo. The implantable endoprosthesis may include an axially flexible structure including a plurality of the elongate elements which are interwoven in a braid-like configuration.

The invention also relates to a temporary radiopaque marker. The marker includes an elongate marker having a proximal end, a distal end, an average thickness of from about 20 microns to about 500 microns, and includes a radiopaque material having a linear attenuation coefficient of from about 10 $cm^{-1}$ at 50 KeV to about 120 $cm^{-1}$ at 50 KeV. The marker is adapted to be removably attached to an implantable endoprosthesis. The proximal end of the marker may include a hook, knob, or eyelet.

The invention also relates to in combination, a discrete radiopaque marker and implantable endoprosthesis. The implantable endoprosthesis has one or more attachment areas and is adapted to be disposed in a body lumen. One or more elongate markers have a proximal end, a distal end, and one or more portions therebetween. The markers have a thickness of from about 20 microns to about 500 microns and include a radiopaque material having a linear attenuation coefficient of from about 10 $cm^{-1}$ at 50 KeV to about 120 $cm^{-1}$ at 50 KeV. The one or more portions of the marker are deformed and permanently disposed about the one or more attachment areas of the endoprosthesis. The markers may be deformed by plastic deformation, elastic deformation, or combinations thereof. The marker may include a twist, knot, crimp, weld, and combinations thereof. The one or more portions may be ductile. The marker may be a spring. The deformation of one or more portions of the marker into an attachment position on the attachment area thereby prevents the marker from releasing from the implantable endoprosthesis.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 2 is a side view of the delivery system and a deployed retrievable radiopaque marker and implantable endoprosthesis in a body lumen;

FIG. 3 is a side view of one possible arrangement of a retrievable radiopaque marker being retrieved from a deployed implantable endoprosthesis in a body lumen;

FIG. 5 is a side view of a retrievable radiopaque marker disposed on an implantable endoprosthesis;

FIG. 6 is a side view of a retrievable radiopaque marker disposed in a helical pattern about the perimeter of an implantable endoprosthesis;

FIGS. 11a–11c are side views of three alternative radiopaque markers;

FIG. 13 is the detail bounded by the dashed-line circle in FIG. 12 illustrating a radiopaque marker disposed around one implantable endoprosthesis wire crossing point;

FIG. 14 is a side view illustrating a discrete radiopaque marker; and

FIG. 15 illustrates the discrete radiopaque marker positioned on an embolization occlusion coil intravascular device.

DETAILED DESCRIPTION OF THE INVENTION

Figure 1:
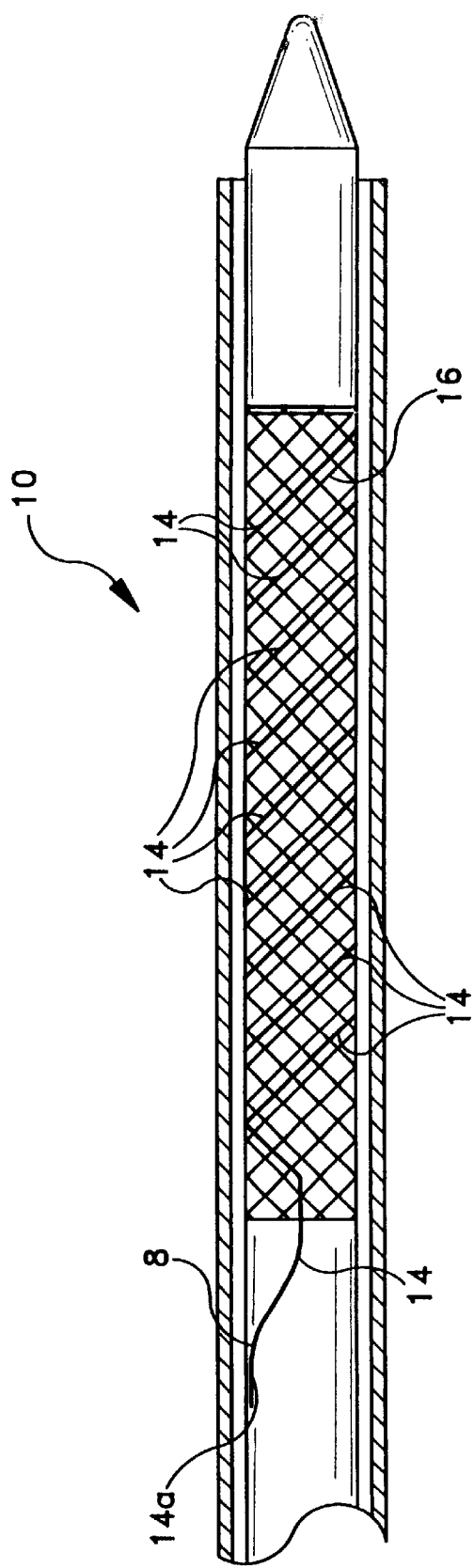
FIG. 1 is a side view of an implantable endoprosthesis delivery system including a retrievable radiopaque marker disposed on an implantable endoprosthesis.

Reference is made to FIGS. 1–3 which illustrate a stent delivery device 10 in various stages of deployment having one or more retrievable markers 14 disposed on an implantable endoprosthesis 16. The retrievable radiopaque markers 14 are disposed on the endoprosthesis 16 preferably before loading into the outer tube of a delivery device 10. Reference is made to a delivery device shown in U.S. Pat. No. 5,026,377.

Figure 8:
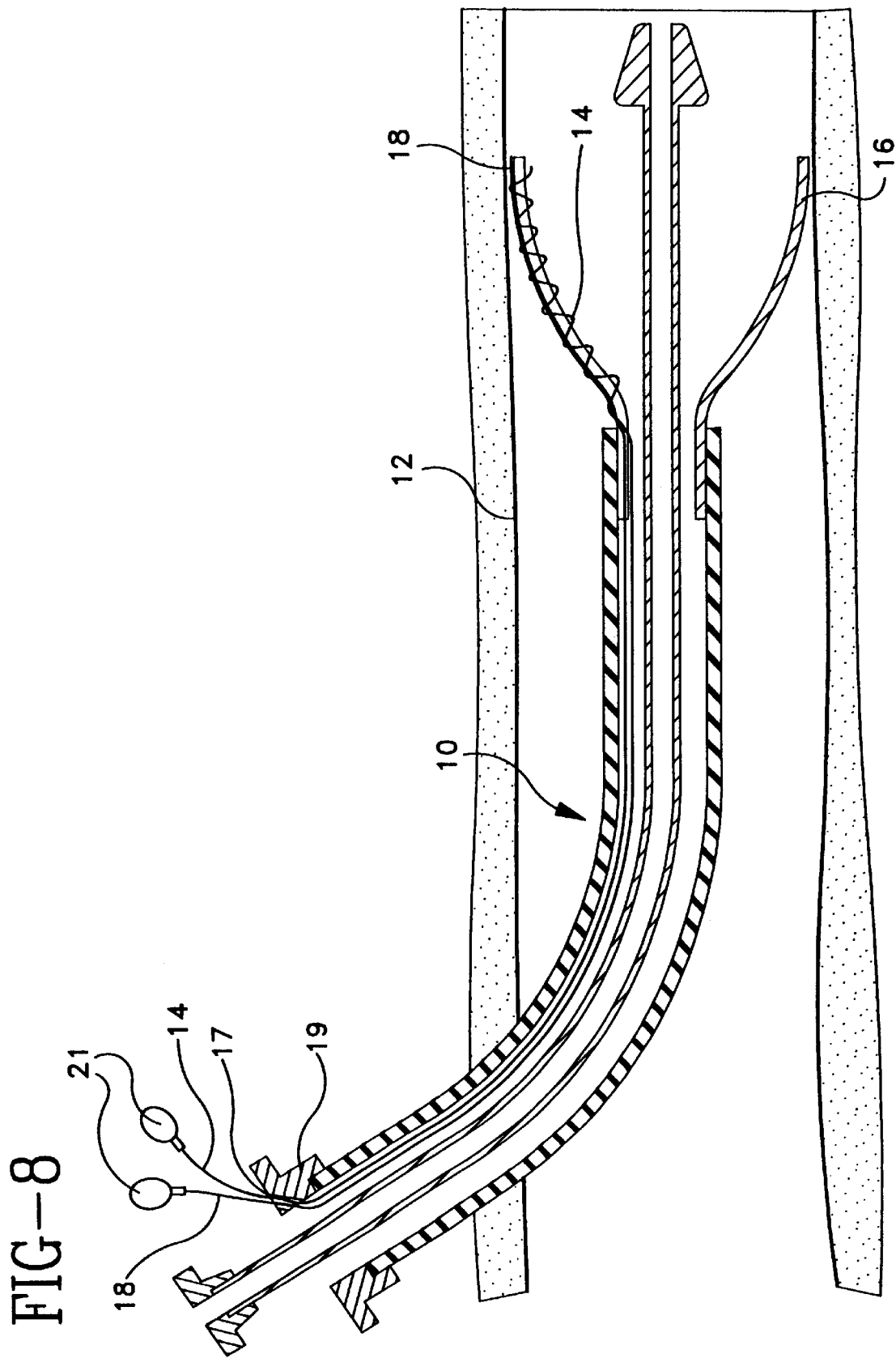
FIG. 8 is a side view of a delivery device illustrating one arrangement of a wire and retrievable radiopaque marker.

As shown in FIG. 1, a proximal end 14a of the retrievable radiopaque marker 14 may be attached at portion 8 which is on the outside surface of the inner tube of a delivery device 10 and an area proximal of the proximal end of the implantable endoprosthesis 16. Other attachment areas are also possible on the delivery device 10. Attachment of the proximal end 14a of the retrievable radiopaque marker 14 to the delivery device may be made by mechanical (e.g., clamp or frictional contact on the surface, interweaving to components in the device, or tying), thermal (e.g. metal or polymer welding), or chemical (e.g., adhesive or gel bond) fastening systems. A predetermined length of the retrievable radiopaque marker 14 may be gathered at or around portion 8 to allow the implantable endoprosthesis 16 to deploy from the delivery device 10. Alternatively, as illustrated in FIG. 8, the retrievable radiopaque marker 14 may be disposed on the implantable endoprosthesis 16, be disposed in a channel or lumen of the delivery device 10, and exit out a port 17 in the hub 19 and be attached to handle 21. The handle 21 may be a ring or a similar shape device adapted to be grasped and aid in retrieval and manipulation of the retrievable radiopaque marker 14 or straight wire 18. Once the implantable endoprosthesis 16 is implanted, the retrievable radiopaque marker 14 may be removed proximally from the body by a force in the proximal direction transmitted to the handle 21. Table 2 lists preferred embodiments of the invention.

TABLE 2

| Marker Type | Description | Function | Devices | Preferred Marker Metal Radiopaque Agents | Preferred Marker Organic Radiopaque Agents | Preferred Marker Matrix Materials |
|---|---|---|---|---|---|---|
| Retrievable, Temporary | threading on helix | mark overall stent length, location in vessel | braided tubular stents, filters, occlusion, valves | Ti, Ta, Zr, Pt | Br, I, Ba, Bi | Polyethylene, silicone, stainless steel, Elgiloy ® |
| Retrievable, Temporary | threading around circumference | mark stent ends, location in vessel, covering length, expansion | braided tubular stents, filters, occlusion, valves, stent grafts | Ti, Ta, Zr, Pt | Br, I, Ba, Bi | Polyethylene, silicone, stainless steel, Elgiloy ® |
| Retrievable, Temporary | threading on straight axial line | mark overall stent length, location in vessel | braided tubular stents, filters, occlusion, valves, stent grafts | Ti, Ta, Zr, Pt | Br, I, Ba, Bi | Polyethylene, silicone, stainless steel, Elgiloy ® |
| Retrievable, Temporary | spring | mark overall stent length, location in vessel, expansion | braided tubular stents, filters, occlusion, valves, stent grafts | Ti, Ta, Zr, Pt | Br, I, Ba, Bi | Polyethylene, silicone, stainless steel, Elgiloy ® |
| Discrete, Permanent | pigtail rings | mark stent ends or center, location in vessel, expansion | braided tubular stents, filters, occlusion, valves, stent grafts | Ti, Ta, Zr, Pt | Br, I, Ba, Bi | Polyethylene, silicone, stainless steel, Elgiloy ® |
| Discrete, Permanent | coils | mark stent ends or center, location in vessel, expansion | braided tubular stents, filters, occlusion, valves, stent grafts | Ti, Ta, Zr, Pt | Br, I, Ba, Bi | Polyethylene silicone, stainless steel, Elgiloy ® |
| Discrete, Permanent | knots | mark stent ends or center, location in vessel, expansion | braided tubular stents, filters, occlusion, valves, stent grafts | Ti, Ta, Zr, Pt | Br, I, Ba, Bi | Polyethylene, silicone, stainless steel, Elgiloy ® |

For description purposes, the markers of the invention can be segregated into types; retrievable temporary and discrete permanent markers. A retrievable temporary marker is generally a strand or strands of material having radiopacity which is loosely or removably incorporated within the implantable device and which can be removed from the device sometime after implantation by pulling on a free end of the marker or by having the marker extend beyond the device to an attachment point on the delivery system or extend through the delivery system and out of the body where it can be grabbed and pulled free of the implant. A discrete permanent marker is generally a strand of material having radiopacity which is securely attached to the implantable device and does not significantly extend away from the device.

An example of a retrievable temporary marker is a radiopaque strand of material loosely passed through or threaded into a braided tubular stent with an end of marker extending away from the stent and attached to the inner tube of the coaxial tube delivery system. As the stent is deployed from the delivery system the marker is used to locate the position of the stent with regard to the stricture. After stent deployment, the delivery system is normally pulled out of the body along the guidewire. The radiopaque marker would be pulled free of the stent as the delivery system is retrieved.

An example of a discrete permanent marker is a coil, knot, or ring of tantalum wire around a feature of a stent, such as a stent wire crossing point. The tantalum wire is wrapped, coiled, or tied around the stent wire and thereby is permanently mechanically attached to the device. The tantalum wire ends are clipped off such that the marker is present as a small, tight ring around a feature of the stent. The stent with the attached markers is loaded and deployed from the delivery system and the markers are not retrieved when the delivery system is removed.

The function of the retrievable radiopaque marker is to temporarily indicate on a radiographic image the location of the stent within the treatment site and the length of the expanded stent can be determined by measuring the length of the marker as it follows the stent shape if the marker was threaded along a stent wire helix or axially along a line in the stent. The marker can be threaded circumferentially at each end of the stent covering in a covered stent or stent-graft to indicate the location of the radiolucent covering material. The stent expansion during deployment can be observed radiographically by watching the radiopaque marker helical or circumferential strand open up as the self-expanding stent is released from its radially constrained state.

Discrete markers have the same functional purpose as the retrievable markers, but they can be more easily used to mark the specific locations of features of interest on the stent. For example, a discrete marker can be added to the center of the stent length to aid the physician in centering the stent within the stricture. Discrete markers could be used to attach covering fabrics or films to stents to make stent grafts so that the location of the covering on the stent could be determined radiographically.

The retrievable and discrete markers can be made from biocompatible metal wires containing elements with relatively high atomic numbers such as titanium, tantalum, zirconium, and platinum. The radiopaque elements can be added by metallurgically alloying or by making clad composite structures. Another type of marker would be to combine titanium, tantalum, zirconium, or platinum metal or oxide powder with a polymer matrix. Polyethylene or silicone are examples of biocompatible polymers that could be used as a matrix material. Combination could be performed by compounding with the polymer resin or coating. Organic radiopaque powders containing elements or salts or oxides of elements such as bromine, iodine, iodide, barium, and bismuth could be used instead of metal powders.

EXAMPLE 1

A retrievable, temporary radiopaque marker can be in the form of a strand of metal or polymer containing radiopaque elements, oxides, or salts of elements with atomic numbers in the range of from about 22 to about 83 loosely threaded along a helical, circumferential, or axial orientation in an endoprosthesis such as a stent, stent-graft, graft, filter, occlusive device, and valve with a free end of the marker extending out from the endoprosthesis such that it is attached to the delivery system or passed outside of the body and the marker and is separated from the implanted endoprosthesis by pulling it free and out of the body. The radiopaque material has a linear attenuation coefficient of from about 10 $cm^{-1}$ at 50 KeV to about 120 $cm^{-1}$ at 50 KeV.

EXAMPLE 2

A retrievable, temporary radiopaque marker can be in the form of a strand of metal or polymer containing radiopaque elements, oxides, or salts of elements with atomic numbers in the range of from about 22 to about 83 formed into a spring and disposed within an endoprosthesis such as a stent, stent-graft, graft, filter, occlusive device, and valve with a free end of the marker extending out from the endoprosthesis such that it is attached to the delivery system or passed outside of the body and the marker and is separated from the implanted endoprosthesis by pulling it free and out of the body. The radiopaque material has a linear attenuation coefficient of from about 10 $cm^{-1}$ at 50 KeV to about 120 $cm^{-1}$ at 50 KeV.

EXAMPLE 3

A retrievable, temporary radiopaque marker can be in the form of a strand of ductile metal wire, ribbon, or braided wire containing radiopaque metallic elements with atomic numbers in the range of from about 22 to about 83, preferably titanium, tantalum, zirconium, and platinum disposed within an endoprosthesis such as a stent, stent-graft, graft, filter, occlusive device, and valve with a free end of the marker extending out from the endoprosthesis such that it is attached to the delivery system or passed outside of the body and the marker and is separated from the implanted endoprosthesis by pulling it free and out of the body. The radiopaque material has a linear attenuation coefficient of from about 10 $cm^{-1}$ at 50 KeV to about 120 $cm^{-1}$ at 50 KeV.

EXAMPLE 4

A retrievable, temporary radiopaque marker can be in the form of a strand of ductile metal wire, ribbon, or braided wire containing radiopaque metallic elements with atomic numbers in the range of from about 22 to about 83, preferably titanium, tantalum, zirconium, and platinum coated or clad composite stainless steel or Elgiloy® wire disposed on an endoprosthesis such as a stent, stent-graft, graft, filter, occlusive device, and valve with a free end of the marker extending out from the endoprosthesis such that it is attached to the delivery system or passed outside of the body and the marker is separated from the implanted endoprosthesis by pulling it free and out of the body. The radiopaque material has a linear attenuation coefficient of from about 10 $cm^{-1}$ at 50 KeV to about 120 $cm^{-1}$ at 50 KeV.

EXAMPLE 5

A retrievable, temporary radiopaque marker can be in the form of a strand of ductile polyethylene or silicone polymer monofilament, ribbon, or multifilament wire containing radiopaque metallic elements with atomic numbers in the range of from about 22 to about 83, preferably compounded or coated with titanium, tantalum, zirconium, and platinum metal powders or bromine, iodine, iodide, barium, and bismuth element, oxides or salts disposed within an endoprosthesis such as a stent, stent-graft, graft, filter, occlusive device, and valve with a free end of the marker extending out from the endoprosthesis such that it is attached to the delivery system or passed outside of the body and the marker and is separated from the implanted endoprosthesis by pulling it free and out of the body. The radiopaque material has a linear attenuation coefficient of from about 10 cm$^{-1}$ at 50 KeV to about 120 cm$^{-1}$ at 50 KeV.

EXAMPLE 6

A retrievable, temporary radiopaque marker can be in the form of a ductile polymer or metal matrix composite wire containing radiopaque metallic elements with atomic numbers in the range of from about 22 to about 83, preferably titanium, tantalum, zirconium, and platinum metal powders or bromine, iodine, iodide, barium, and bismuth element, oxides or salt powders disposed within an endoprosthesis such as a stent, stent-graft, graft, filter, occlusive device, and valve with a free end of the marker extending out from the endoprosthesis such that it is attached to the delivery system or passed outside of the body and the marker and is separated from the implanted endoprosthesis by pulling it free and out of the body. The radiopaque material has a linear attenuation coefficient of from about 10 cm$^{-1}$ at 50 KeV to about 120 cm$^{-1}$ at 50 KeV.

EXAMPLE 7

A discrete, permanent radiopaque marker can be in the form of a ductile metal wire, ribbon, or braided wire containing radiopaque metallic elements with atomic numbers in the range of from about 22 to about 83, preferably titanium, tantalum, zirconium, and platinum attached by wrapping, coiling, or tying around features within an endoprosthesis such as a stent, stent-graft, graft, filter, occlusive device, and valve such that the marker stays permanently attached by mechanical or adhesive forces to the endoprosthesis during deployment from the delivery system for the life of the implant. The radiopaque material has a linear attenuation coefficient of from about 10 cm$^{-1}$ at 50 KeV to about 120 cm$^{-1}$ at 50 KeV.

EXAMPLE 8

A discrete, permanent radiopaque marker can be in the form of a strand of ductile metal wire, ribbon, or braided wire containing radiopaque metallic elements with atomic numbers in the range of from about 22 to about 83, preferably titanium, tantalum, zirconium, and platinum coated or clad composite stainless steel or Elgiloy® wire ductile metal wire, ribbon, or braided wire containing radiopaque metallic elements with atomic numbers in the range of from about 22 to about 83, preferably titanium, tantalum, zirconium, and platinum attached by wrapping, coiling, or tying around features within an endoprosthesis such as a stent, stent-graft, graft, filter, occlusive device, and valve such that the marker stays permanently attached by mechanical or adhesive forces to the endoprosthesis during deployment from the delivery system for the life of the implant. The radiopaque material has a linear attenuation coefficient of from about 10 cm$^{-1}$ at 50 KeV to about 120 cm$^{-1}$ at 50 KeV.

EXAMPLE 9

A discrete, permanent radiopaque marker can be in the form of a strand of ductile polyethylene or silicone polymer monofilament, ribbon, or multifilament wire containing radiopaque metallic elements with atomic numbers in the range of from about 22 to about 83, preferably compounded or coated with titanium, tantalum, zirconium, and platinum metal powders or bromine, iodine, iodide, barium, and bismuth element, oxides or salts attached by wrapping, coiling, or tying around features within an endoprosthesis such as a stent, stent-graft, graft, filter, occlusive device, and valve such that the marker stays permanently attached by mechanical or adhesive forces to the endoprosthesis during deployment from the delivery system for the life of the implant. The radiopaque material has a linear attenuation coefficient of from about 10 cm$^{-1}$ at 50 KeV to about 120 cm$^{-1}$ at 50 KeV.

FIGS. 2–3 illustrate an implantable endoprosthesis 16 in a body lumen 12. Implantable endoprostheses known in the art include stents, stent-grafts, grafts, filters, occlusive devices, and valves, all of which may incorporate the retrievable radiopaque marker 14 or discrete marker.

Figure 4C:
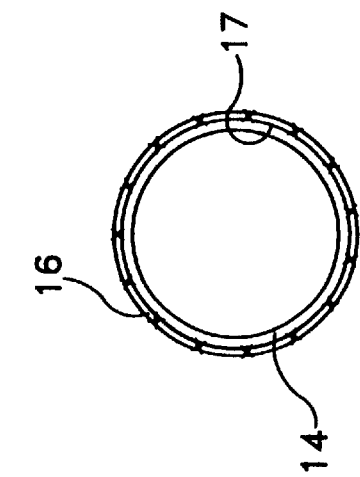
FIGS. 4a, 4b, and 4c are cross-sectional views of three alternative marker dispositions on an implantable endoprosthesis at section 4—4 of FIG. 2.
Figure 4B:
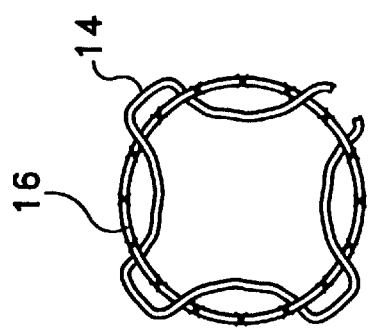
Figure 4A:
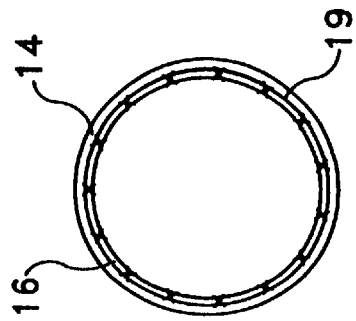

FIGS. 4a–4c illustrate three alternative locations on an implantable endoprosthesis 16 for disposing the retrievable radiopaque marker 14. The retrievable radiopaque marker 14 may be an elongate element including a thread, filament, or ribbon such as a highly radiopaque wire relatively loosely woven into or wrapped around the inside, outside, or ends of the implantable endoprosthesis 16.

Reference is made to FIGS. 5–6 illustrating the retrievable radiopaque marker 14 disposed in two alternative patterns on the implantable endoprosthesis 16. FIG. 5 shows the marker 14 interwoven or interbraided loosely along the longitudinal axis of the endoprosthesis 16. FIG. 6 shows the marker 14 disposed in a helical pattern about the implantable endoprosthesis 16. Other patterns and dispositions of the marker 14 on the endoprosthesis 16 are also possible. One or more markers 14 may be temporarily disposed on the implantable endoprosthesis 16 in alternative patterns to advantageously provide temporary radiopacity to predetermined locations on the implantable endoprosthesis 16.

The retrievable radiopaque marker 14 may be applied temporarily to one or more surfaces of the implantable endoprosthesis 16 with a relatively weak bioabsorbable adhesive or gelatin, for instance, as shown in FIGS. 4a and 4c. Alternatively, the retrievable radiopaque marker 14 may be formed into a spring having spring force characteristics and be applied on the inside surface of the implantable endoprosthesis 16 as shown in FIG. 4c. Spring force allows the retrievable radiopaque marker 14 to press against the interior of the implantable endoprosthesis 16 and provide temporary radiopacity thereto.

The retrievable radiopaque marker 14 may be braided to form a rope or cable. The retrievable radiopaque marker 14 may be woven or inter-braided into the implantable endoprosthesis 16 during manufacture.

As the implantable endoprosthesis 16 is deployed from the delivery device 10, the retrievable radiopaque marker 14 may adjust with expansion of the implantable endoprosthesis 16 and thereby advantageously provides radiopacity and viewing of the implantable endoprosthesis 16 position or size during fluoroscopy. Once the implantable endoprosthesis 16 is fully deployed, the delivery device 10 and the retrievable radiopaque marker 14 may be removed from the body. For example, one end of the retrievable radiopaque marker 14 may be attached to the delivery device 10 and the other end may be disposed at predetermined locations on the implantable endoprosthesis 16. As the delivery device 10 is withdrawn, the retrievable radiopaque marker 14 may be pulled away from implantable endoprosthesis 16 and removed from the body. The retrievable radiopaque marker 14 may be loosely incorporated into the implantable endoprosthesis 16 and be easily retrieved without disturbing the implantable endoprosthesis 16 or body tissue. Alternatively, the retrievable radiopaque marker 14 may remain on the implantable endoprosthesis 16 for a period of time if there is a need for follow-up angiography, and then be ultimately removed.

Figure 7:
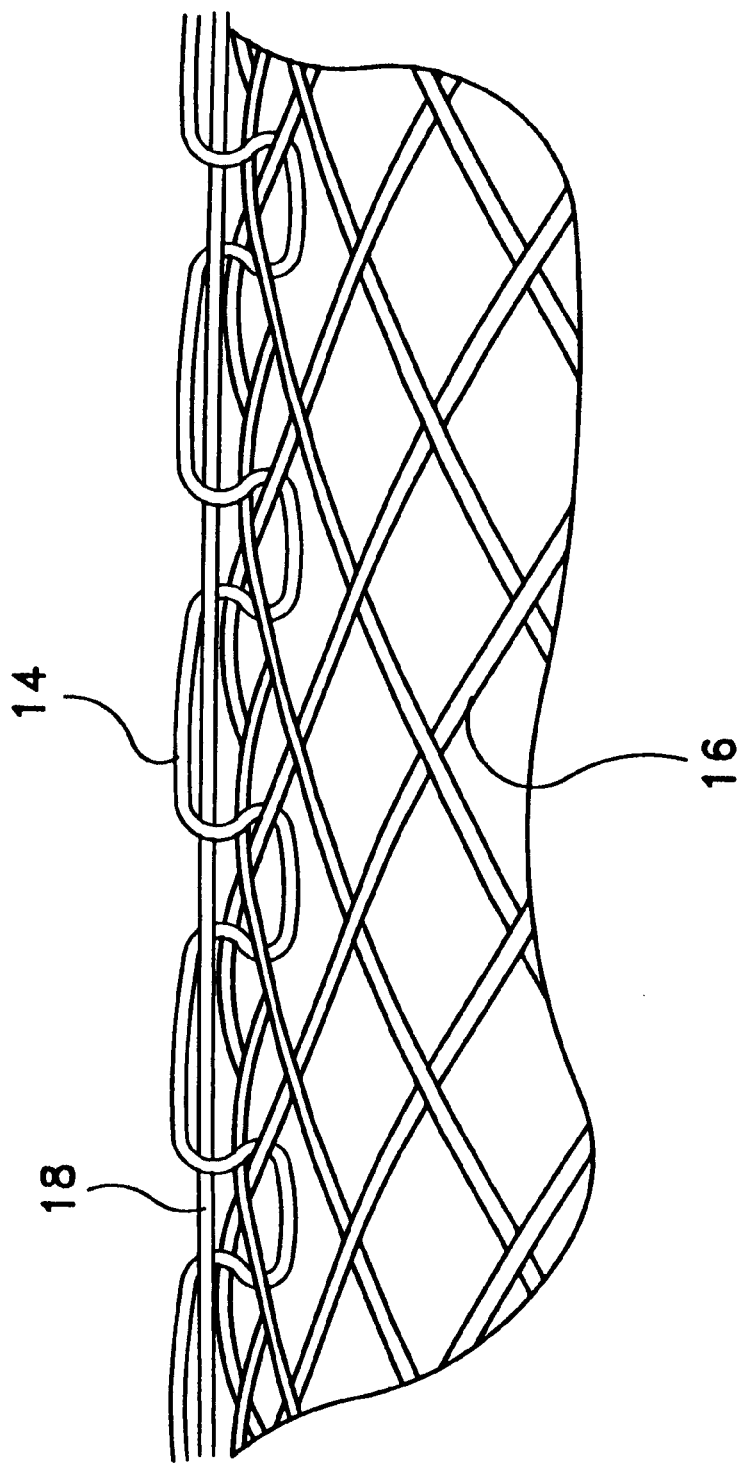
FIG. 7 is a side view illustrating one possible arrangement of a straight wire and retrievable radiopaque marker disposed on an implantable endoprosthesis.

Reference is made to FIGS. 7–8 illustrating an alternative embodiment including a retrievable radiopaque marker 14 and wire 18. The wire 18 is used to prevent removal of the marker 14 without first removal of the wire 18. The retrievable radiopaque marker 14 is relatively loosely woven or inter-braided in and out of the implantable endoprosthesis 16, and is maintained in place by another relatively straight, flexible and adjacent movable wire 18. The marker 14 and wire 18 may be made by various methods and materials including polymers, metals, ceramics, or similar materials.

The wire 18 may be placed inside, outside, or penetrate between filaments of the implantable endoprosthesis 16. The wire 18 and retrievable radiopaque marker 14 are disposed at desired predetermined areas and in various patterns on the implantable endoprosthesis 16. Various combinations of the wire 18 and retrievable radiopaque marker 14 are possible including multiple markers 14 or wires 18. As illustrated in FIG. 8, the retrievable radiopaque marker 14 and wire 18 may be disposed on the implantable endoprosthesis 16, be disposed in a channel or lumen of the delivery device 10, and exit out a port 17 in the hub 19 and be attached to handle 21. The handle 21 may be a ring or a similar shape device adapted to be grasped and aid in retrieval and manipulation of the retrievable radiopaque marker 14. Once the implantable endoprosthesis 16 is implanted, the wire 18 may be removed proximally by a force which liberates the retrievable radiopaque marker 14 and allows removal thereof.

A limited amount of interweaving or interbraiding of the retrievable radiopaque marker 14 or wire 18 is generally desired in order to minimize the force required for retrieval. The retrievable radiopaque marker 14 or wire 18 may be coated with a biocompatible material having a low coefficient of friction for ease of removal from the implantable endoprosthesis 16.

Figure 9:
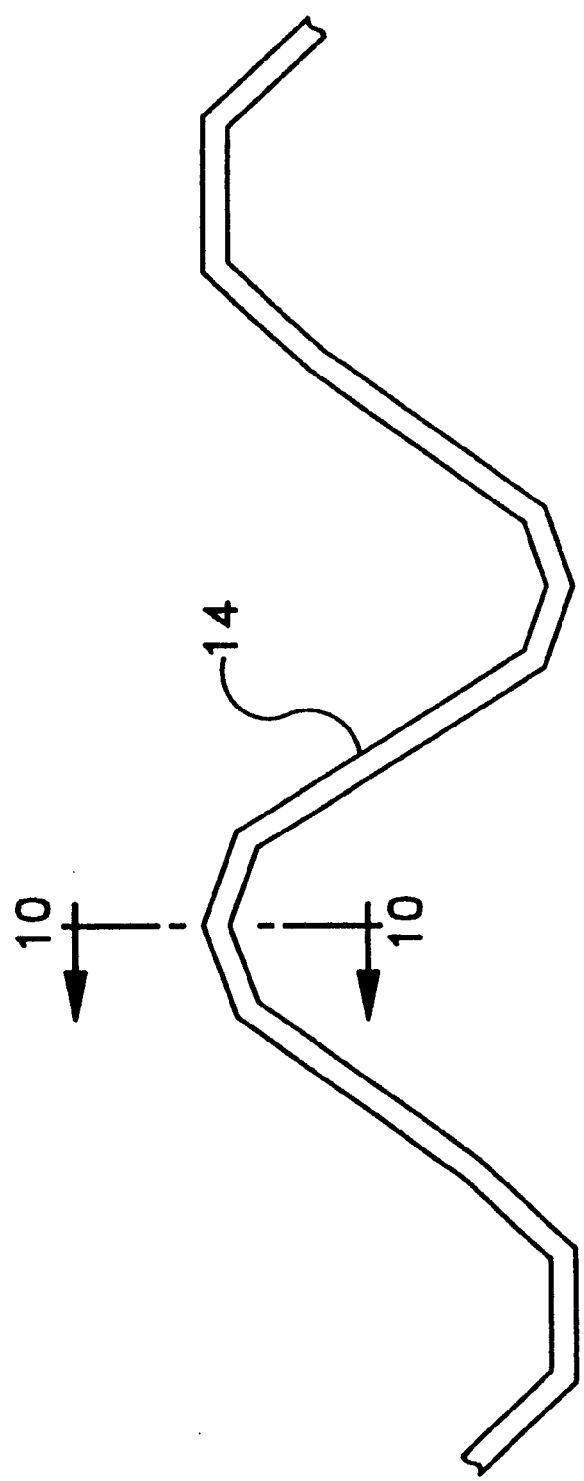
FIG. 9 is a side view of a relatively flexible retrievable radiopaque marker.

Reference is made to FIG. 9 illustrating a retrievable radiopaque marker 14 preferably made from a relatively flexible wire, suture, filament, ribbon, braided wires, or combinations thereof including radiopaque material such as a metal, metallic alloy, or polymer containing a material that is highly radiopaque.

Figure 10A:
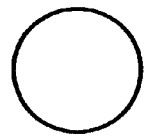
FIGS. 10a–10e are cross-sectional views of five alternative radiopaque markers at section 10—10 of FIG. 9.
Figure 10B:
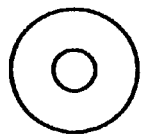
Figure 10C:
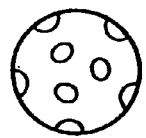
Figure 10D:
Figure 10E:
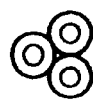

FIGS. 10a–10e illustrate alternative cross-sectional embodiments of the retrievable radiopaque marker 14 taken through the line 10—10 of FIG. 9. FIG. 10a shows a substantially solid member; FIG. 10b shows a hollow member; FIG. 10c shows a member having pores extending radially into the member; FIG. 10d shows a rectangular or ribbon member; and FIG. 10e shows a braided hollow member. FIG. 10e may also be a substantially solid braided member.

A composite radiopaque marker 14 may be made from materials coated or compounded with a radiopaque substance such as iodine, zirconium oxide, barium sulfate, bismuth trioxide, or a related oxide or salt substance. Composite radiopaque materials may be a radiopaque material containing at least one element having an atomic number, preferably higher than about 22. Another radiopaque marker 14 may include gold, platinum, metal, tantalum, metallic alloy, or a polymer containing a radiopaque filler such as barium sulfate, bismuth trioxide, iodine, iodide, or like materials.

Figure 11C:
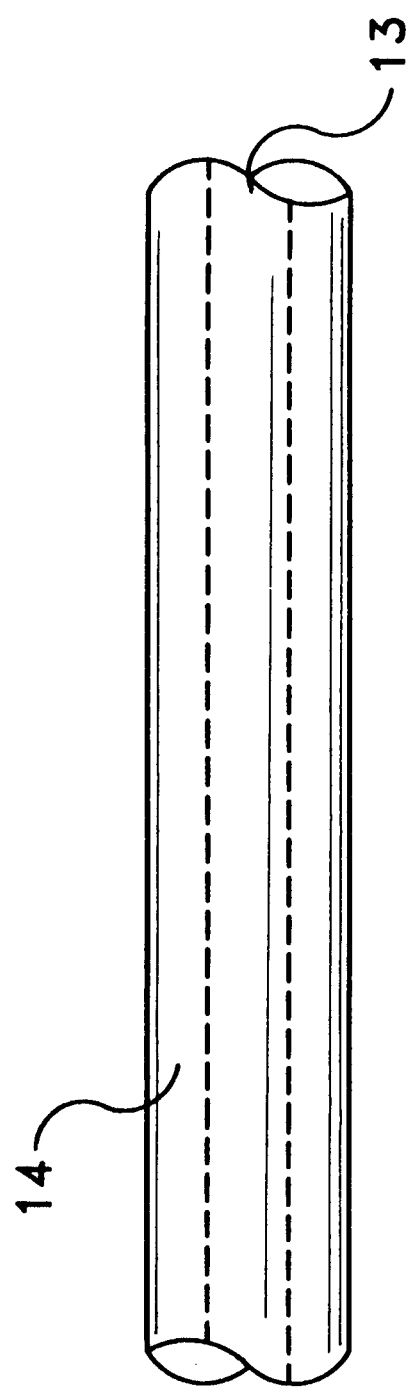

Reference is made to FIGS. 11a–11c illustrating alternative embodiments of a portion of the retrievable radiopaque marker 14. The retrievable radiopaque marker 14 may have at least one hollow portion 15 which extends throughout the marker 14 for temporary or permanent containment of a retrievable radiopaque material. For example, a radiopaque core 13 as shown in FIG. 11c may be disposed in and retrieved from a hollow portion 15 in the retrievable radiopaque marker 14. One end of the radiopaque core 13 may be attached to the delivery device 10 by a wire or the like and removed from the retrievable radiopaque marker 14 and body lumen by a force originating from outside the body. The outside case of the marker 14 may remain disposed on the implantable endoprosthesis 16 or be removed therefrom. The temporary radiopaque core 13 may be solid or include a casing surrounding a solid, gel, powder, or combination thereof and be held in place with a relatively weak bioabsorbable adhesive gelatin, friction, or by other mechanical or chemical means known in the art in a hollow 15, cavity, or porous portion. The temporary radiopaque core 13 preferably is made of a radiopaque material that has a linear attenuation coefficient of from about 10 $cm^{-1}$ at 50 KeV to about 120 $cm^{-1}$ at 50 KeV and is adapted to be removably attachable in at least one hollow 15, cavity, or porous portion in the marker 14. Alternatively, the core 13 may remain in the hollow 15, cavity, or porous portion of the marker 14 and be removed when the marker 14 is retrieved from the body. In alternative embodiments, one or more closed cavities within the marker 14 or pores on the surface as shown in FIG. 10c or pores extending through to a hollow or cavity portion within the marker 14 (not shown) may be utilized for temporary or permanent containment of a retrievable radiopaque materials or be utilized for a passageway for dispersal of the radiopaque materials contained in the marker 14 into the body.

Figure 12:
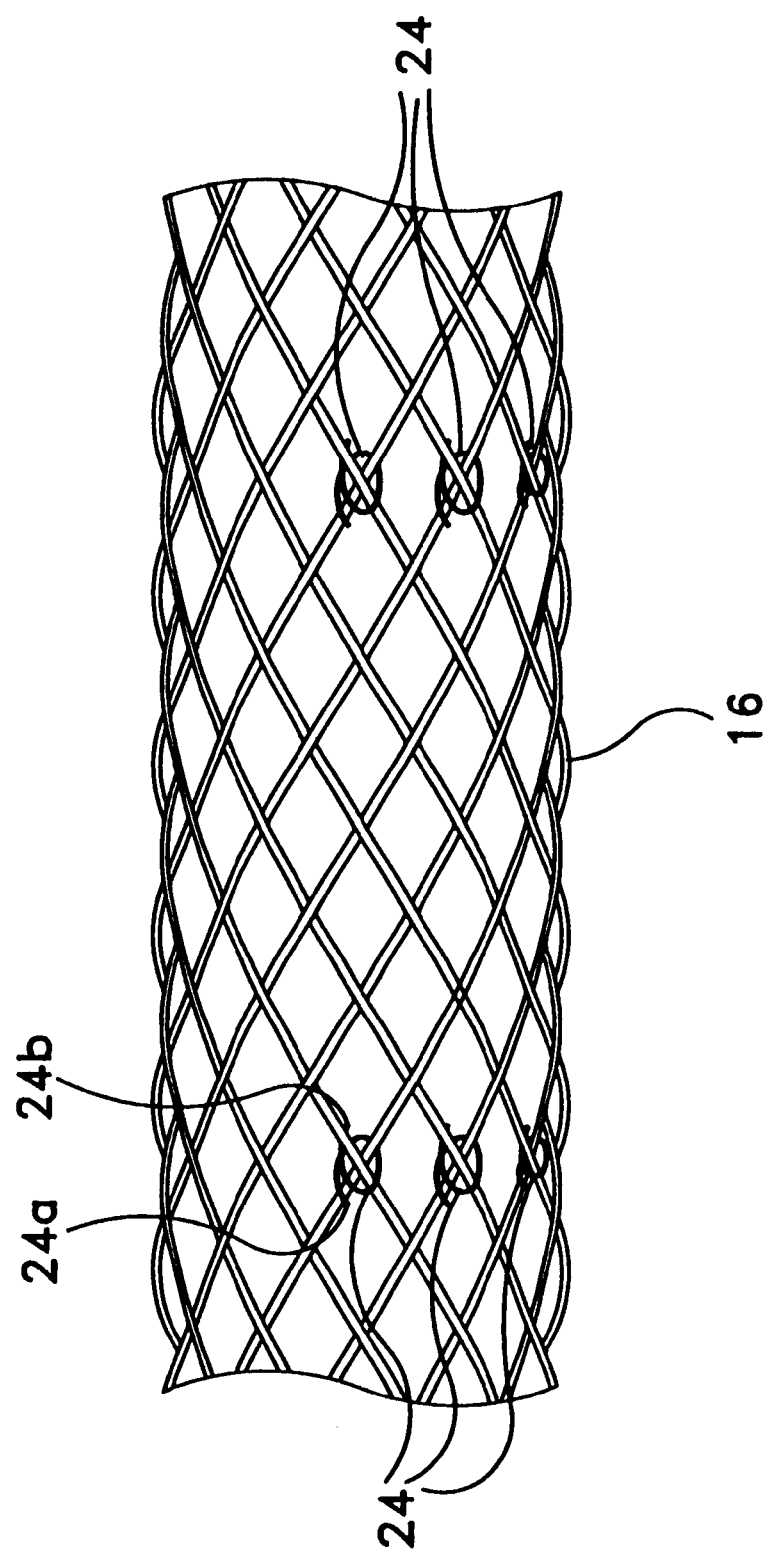
FIG. 12 is a side view illustrating one possible arrangement of discrete radiopaque markers disposed on an implantable endoprosthesis.

FIG. 12 illustrates discrete radiopaque markers 24 made by forming small rings or coils of radiopaque wire around features of the implantable endoprosthesis 16. Relatively small and discrete wire loop (pigtail) radiopaque markers 24 are shown at the wire crossing points on the tubular braid.

FIG. 13 illustrates the detail bounded by the dashed-line circle in FIG. 12 showing a radiopaque wire loop marker 24 around one implantable endoprosthesis 16 wire crossing point.

FIG. 14 illustrates the marker 24 of FIG. 12 and FIG. 13 and shows wire ends 24a, 24b which simply pass over each other to form an enclosed loop or overlap. The discrete radiopaque markers 24 may be plastically or elastically deformable. The markers 24 may be springs or spring-like for attachment purposes. Alternatively, the ends 24a, 24b may be tied, knotted, crimped, spot welded, or bent. The markers 24 may be relatively small and comprise a single loop or pigtail of wire around one filament crossing point, filament, an embolization coil, or the like. The marker 24 is preferably made of a biocompatible radiopaque material that is ductile including pure tantalum, platinum, gold, zirconium, niobium, titanium, stainless steel, or combinations thereof.

The marker 24 may be a pig-tail, coil, or knot design and is preferably formed from an elongate member such as a wire and shaped accordingly onto the implantable endoprosthesis 16. The marker 24 advantageously allows custom marking of the implantable endoprosthesis 16 without the need to acquire preformed marker bands or to devise a complicated manufacturing operation such as swaging, threading, or braiding. The discrete radiopaque markers 24 may be easily and quickly added to the implantable endoprosthesis 16. Also, only small, specific sites are marked by the marker 24 so a minimum amount of foreign body material would be added to the implantable endoprosthesis 16. The discrete radiopaque markers 24 may be used on an implantable endoprosthesis 16 made of a bioabsorbable polymer including polylactide.

The markers 14, 24 should preferably be smaller than the size of the element in the implantable endoprosthesis 16. The size of the markers 14, 24 is also dependent on the type of radiopaque material used. For example, tantalum wire (0.006' diameter, hard drawn) may be used. The smaller diameter wire fits through most weaves, is deformable, and may be cut to size.

Reference is made to FIGS. 12–13 illustrating discrete markers 24 looped one or more times about a filament or filament crossing point to prevent release therefrom. The ends 24a, 24b are clipped and positioned to lie in a plane parallel to the longitudinal axis of the implantable endoprosthesis 16. The marker 24 may be disposed on one or more filament crossing or every other filament crossing point around the circumference of the braid in one circular transverse plane. The markers 24 may be positioned to form one or more circumferential rings on the implantable endoprosthesis 16. Alternatively, the markers 24 may be positioned along an embolization occlusion coil intravascular device or filament at predetermined locations as illustrated in FIG. 15. The marker 24 may be plastically deformed and the marker ends 24a, 24b may be looped one or more times about a portion of the implantable endoprosthesis 16 and then pulled to provide a snug disposition. The ends 24a, 24b may then be tied, twisted, knotted, welded or adhesively connected together and thereafter clipped and positioned to lie in an unobtrusive low-profile position.

It will be evident from considerations of the foregoing that the retrievable radiopaque marker 14 and discrete radiopaque marker 24 may be constructed using a number of methods and materials, in a wide variety of sizes and styles for the greater efficiency and convenience of a user.

A bioabsorbable marker that may advantageously be used in conjunction with the present invention is disclosed in J. Stinson's U.S. patent application entitled "Bioabsorbable Marker Having Radiopaque Constituents And Method Of Using Same", Ser. No. 08/904,951, filed concurrently herewith, and commonly assigned to the assignee of this application.

A bioabsorbable stent that may advantageously be used in conjunction with the present invention is disclosed in J. Stinson's United States patent application entitled "Bioabsorbable Implantable Endoprosthesis With Reservoir And Method Of Using Same", U.S. Pat. No. 5,980,564 filed concurrently herewith, and commonly assigned to the assignee of this application.

Another bioabsorbable stent that may advantageously be used in conjunction with the present invention is disclosed in J. Stinson's U.S. patent application entitled "Bioabsorbable Self-Expanding Stent", Ser. No. 08/904,467 filed concurrently herewith, and commonly assigned to the assignee of this application.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. An implantable endoprosthesis and radiopaque marker system comprising:
   an implantable endoprosthesis adapted to be disposed in a body lumen; and
   at least one elongate marker having a proximal end, a distal end, a thickness, and at least one radiopaque portion, the radiopaque portion including a radiopaque material wherein the marker is removably attached to at least a portion of the implantable endoprosthesis and is removeable from the endoprosthesis when the endoprosthesis is in vivo.

2. The implantable endoprosthesis and radiopaque marker system of claim 1 wherein the radiopaque material is at least partially dispersed from the marker over time.

3. The implantable endoprosthesis and radiopaque marker system of claim 1 wherein the radiopaque material has a linear attenuation coefficient of from about 10 cm$^{-1}$ at 50 KeV to about 120 cm$^{-1}$ at 50 KeV.

4. The implantable endoprosthesis and radiopaque marker system of claim 1 wherein the marker has a thickness of from about 20 microns to about 500 microns and the radiopaque material has at least one element with an atomic number of from about 22 to about 83.

5. The implantable endoprosthesis and radiopaque marker system of claim 1 wherein the marker includes an oxide or salt material having at least one element with an atomic number of from about 22 to about 83.

6. The implantable endoprosthesis and radiopaque marker system of claim 1 wherein the marker includes a material selected from the group consisting of barium sulfate, bismuth trioxide, iodine, iodide, titanium oxide, zirconium oxide, gold, platinum, silver, tantalum, niobium, stainless steel, and combinations thereof.

7. The implantable endoprosthesis and radiopaque marker system of claim 1 wherein the marker is coated or alloyed with a radiopaque material that has a linear attenuation coefficient of from about 10 cm$^{-1}$ at 50 KeV to about 120 cm$^{-1}$ at 50 KeV.

8. The implantable endoprosthesis and radiopaque marker system of claim 1 wherein the marker crosses at least one portion of the implantable endoprosthesis.

9. The implantable endoprosthesis and radiopaque marker system of claim 1 wherein the marker is in a form selected from the group consisting of wire, mono-filament, multi-filament, ribbon, suture, spring, and combinations thereof.

10. The implantable endoprosthesis and radiopaque marker system of claim 1 wherein the marker comprises material selected from the group consisting of metal, polymer, copolymer, ceramic, and combinations thereof.

11. The implantable endoprosthesis and radiopaque marker system of claim 1 wherein the marker includes at least one hollow, cavity, or porous portion.

12. The implantable endoprosthesis and radiopaque marker system of claim 1 wherein the marker includes at least one hollow, cavity, or porous portion therein adapted to receive the radiopaque material removably attached therein.

13. The implantable endoprosthesis and radiopaque marker system of claim 1 wherein the proximal end of the marker is connected to at least one of the implantable endoprosthesis delivery device or a handle.

14. The implantable endoprosthesis and radiopaque marker system of claim 1 wherein the proximal end of the marker has a hook, knob, ring, or eyelet attached thereto.

15. The implantable endoprosthesis and radiopaque marker system of claim 1 further comprising a delivery device wherein the implantable endoprosthesis and marker are disposed in the delivery device and adapted for implantation into a body lumen.

16. The implantable endoprosthesis and radiopaque marker system of claim 1 wherein the implantable endoprosthesis is selected from the group consisting of stent, stent-graft, graft, filter, occlusive device, and valve.

17. The implantable endoprosthesis and radiopaque marker system of claim 1 wherein the marker system further comprises at least one elongate wire removably attached to the implantable endoprosthesis wherein the marker crosses at least a portion of the implantable endoprosthesis and crosses the at least one elongate wire.

18. An implantable endoprosthesis and radiopaque marker system comprising:
  an implantable endoprosthesis adapted to be disposed in a body lumen; and
  at least one elongate marker removably attached to the implantable endoprosthesis, the marker having a proximal end, a distal end, a thickness, at least one hollow, cavity, or porous portion, and at least one radiopaque material having a linear attenuation coefficient of from about 10 cm$^{-1}$ at 50 KeV to about 120 cm$^{-1}$ at 50 KeV wherein the radiopaque material is removably attached to at least one of the hollow, cavity, or porous portions.

19. The implantable endoprosthesis and radiopaque marker system of claim 18 wherein the radiopaque portion is at least one of a liquid, solid, powder, gel, wire, monofilament, multi-filament, pellet, particle, and combinations thereof.

20. A method of marking an implantable endoprosthesis comprising the steps of:
  removably-attaching at least one elongate marker having a proximal and distal end to a portion of an implantable endoprosthesis to form an assembly, the marker including at least one radiopaque material having a linear attenuation coefficient of from about 10 cm$^{-1}$ at 50 KeV to about 120 cm$^{-1}$ at 50 KeV;
  disposing the assembly in a delivery system;
  inserting the delivery system in a body lumen;
  deploying the assembly from the delivery system into the body lumen; and
  removing at least a portion of marker from the implantable endoprosthesis.

21. The method of marking an implantable endoprosthesis of claim 20 further comprising the step of performing one or more medical procedures using the markers as a surgical guide prior to removing at least a portion of the marker from the endoprosthesis.

22. The method of marking an implantable endoprosthesis of claim 20 wherein the marker includes a radiopaque portion and a secondary portion and the radiopaque portion is first substantially removed from the implantable endoprosthesis prior to removal of the remaining secondary portion of the marker.

23. The method of marking an implantable endoprosthesis of claim 20 wherein removing the marker from the implantable endoprosthesis is performed by a force controlled from outside the body.

24. The method of marking an implantable endoprosthesis of claim 20 further comprising the steps of removably-attaching at least one wire to at least a portion of the implantable endoprosthesis and crossing the wire or the elongate marker over the other such that one of the marker or the wire requires removal prior to removal of the other from the implantable endoprosthesis.

25. An implantable endoprosthesis and radiopaque marker system comprising:
  an implantable endoprosthesis having a tubular and radially expandable structure adapted to be disposed in a body lumen; and
  at least one elongate marker removably attached to the implantable endoprosthesis, the marker including a radiopaque material having a linear attenuation coefficient of from about 10 cm$^{-1}$ at 50 KeV to about 120 cm$^{-1}$ at 50 KeV, a proximal end, a distal end, and a thickness wherein the marker is adapted to disperse at least a portion of the radiopaque material into the body when in vivo and wherein the marker is removable from the endoprosthesis when the endoprosthesis is in vivo.

26. The implantable endoprosthesis and radiopaque marker system of claim 25 wherein the implantable endoprosthesis further comprises an axially flexible structure including a plurality of the elongate elements which are interwoven in a braid-like configuration.

27. A temporary radiopaque marker comprising:
  an elongate marker having a proximal end, a distal end, an average thickness of from about 20 microns to about 500 microns, and including a radiopaque material having a linear attenuation coefficient of from about 10 cm$^{-1}$ at 50 KeV to about 120 cm$^{-1}$ at 50 KeV wherein the marker is adapted to be removably attached to an implantable endoprosthesis and removable from the endoprosthesis when the endoprosthesis is in vivo.

28. The temporary radiopaque marker of claim 27 wherein the proximal end further comprises at least one of a hook, knob, or eyelet.

29. In combination, a discrete radiopaque marker and implantable endoprosthesis comprising:
  an implantable endoprosthesis having one or more attachment areas and adapted to be disposed in a body lumen; and
  one or more elongate markers having a proximal end, a distal end, and one or more portions therebetween, the markers having a thickness of from about 20 microns to about 500 microns and including a radiopaque material disposed in at least one of a hollow, cavity or porous portion in the one or more elongate markers, the radiopaque material having a linear attenuation coefficient of from about 10 cm$^{-1}$ at 50 KeV to about 120 cm$^{-1}$ at 50 KeV, at least a portion of the one or more elongate markers are made of a ductile material and adapted to be deformed and permanently disposed about the one or more attachment areas of the endoprosthesis.

30. The in combination, discrete radiopaque marker and implantable endoprosthesis of claim 29 wherein the markers are deformed by at least one of plastic deformation, elastic deformation, or combinations thereof.

31. The in combination, discrete radiopaque marker and implantable endoprosthesis of claim 29 wherein the marker further includes one of a twist, knot, crimp, weld, and combinations thereof.

32. The in combination, discrete radiopaque marker and implantable endoprosthesis of claim 29 wherein the marker is a spring.

33. The in combination, discrete radiopaque marker and implantable endoprosthesis of claim 29 wherein the deformation of one or more portions of the marker into an attachment position on the attachment area thereby prevents the marker from releasing from the implantable endoprosthesis.

34. An implantable endoprosthesis and radiopaque marker system including:
  an implantable endoprosthesis adapted to be disposed in a body lumen; and
  an elongate marker removably attached to the endoprosthesis and having a free end extending away from the endoprosthesis, said elongate marker having at least one radiopaque portion including a radiopaque material disposed proximate the endoprosthesis when the marker is so attached thereto, wherein the marker is at least partially removable from the endoprosthesis by pulling said free end away from the endoprosthesis.

35. The system of claim 34 further including:

a delivery device adapted for a delivery of the endoprosthesis to the body lumen and a withdrawal of the delivery device from the body lumen after an implantation of the endoprosthesis; and wherein the free end of the marker is attached to the delivery device whereby the withdrawal of the delivery device pulls the free end to remove the marker from the endoprosthesis.

36. The system of claim 34 wherein:

a portion of the marker is woven into the endoprosthesis.

37. The system of claim 34 further including:

an adhesive for temporarily securing the marker to the endoprosthesis.

38. The system of claim 34 wherein:

said radiopaque material is adapted to be at least partially dispersed from the marker into the body when the endoprosthesis is in vivo.

39. The system of claim 34 wherein:

the radiopaque material includes an element having an atomic number of at least 22.

40. The system of claim 39 wherein:

the radiopaque material includes said element in a form selected from the group consisting of: a metal, a metallic alloy including the element, an oxide including the element, and a salt including the element.

41. The system of claim 39 wherein:

the marker includes a polymer matrix combined with a powder, and the powder includes the element.

42. The system of claim 34 wherein:

the radiopaque material has a linear attenuation coefficient of at least 5.46 cm$^{-1}$ at 50 KeV.

43. The system of claim 34 wherein:

the marker is provided in a form selected from the group consisting of: wires, monofilaments, multi-filaments, ribbons, sutures, springs, and combinations thereof.

44. An implantable endoprosthesis and radiopaque marker system including:

an implantable endoprosthesis adapted to be disposed in a body lumen; and an elongate marker removably attached to the implantable endoprosthesis and having at least one radiopaque portion including a radiopaque material, wherein the radiopaque material is adapted to be at least partially dispersed from the marker into the body when the endoprosthesis is in vivo.

45. The system of claim 44 wherein:

the radiopaque material includes an element having an atomic number of at least 22.

46. The system of claim 45 wherein:

the radiopaque material includes said element in the form of a salt including the element.

47. The system of claim 44 wherein:

the radiopaque material has a linear attenuation coefficient of at least 5.46 cm$^{-1}$ at 50 KeV.

48. The system of claim 44 wherein:

the radiopaque portion of the marker is provided as a coating.

49. The system of claim 44 wherein:

the marker includes a free end extending away from the endoprosthesis when the marker is removably attached thereto, and the marker is removable from the endoprosthesis by pulling the free end away from the endoprosthesis.

50. The system of claim 49 further including:

a delivery device adapted for delivery of the endoprosthesis to the body lumen and a withdrawal of the delivery device from the body lumen after an implantation of the endoprosthesis; and wherein the free end of the marker is attached to the delivery device whereby the withdrawal of the delivery device pulls the free end to remove the marker from the endoprosthesis.

51. The system of claim 44 wherein:

a portion of the marker is woven into the endoprosthesis.

52. The system of claim 44 wherein:

the marker is formed as a spring, and when so removably attached is retained with respect to the endoprosthesis by a spring force.

53. The system of claim 44 further including:

an adhesive for temporarily securing the marker to the endoprosthesis.

54. A process for modifying an implantable endoprosthesis to temporarily enhance a visualization thereof during and after an implantation thereof in a body lumen, comprising:

providing a body implantable endoprosthesis;

providing a marker, each marker having at least one radiopaque portion including a radiopaque material; and prior to an implantation of the endoprosthesis, attaching the marker to the implantable endoprosthesis with a free end of the marker extending away from the endoprosthesis, and further attaching the marker in a manner that facilitates a removal of the marker from the endoprosthesis by pulling the free end away from the endoprosthesis.

55. The process of claim 54 further including:

after attaching the marker to the endoprosthesis, mounting the endoprosthesis releasably to a delivery device.

56. The process of claim 55 further including:

securing the free end of the marker to the delivery device, whereby a withdrawal of the delivery device after an implantation of the endoprosthesis pulls the free end of the marker to remove the marker from the endoprosthesis.

57. The process of claim 54 wherein:

the attaching of the marker to the endoprosthesis comprises using a mode of attachment selected from the group of modes consisting of: weaving a portion of the marker into the endoprosthesis, providing the marker as a spring having a spring force and using the spring force to retain the marker with respect to the endoprosthesis, and using an adhesive to temporarily attach the marker to the endoprosthesis.

* * * * *